United States Patent
Farnum

[11] Patent Number: 5,647,378
[45] Date of Patent: Jul. 15, 1997

[54] INVALID SUPPORT BELT

[76] Inventor: Randal J. Farnum, 930 W. Eula Ct., Glendale, Wis. 53209

[21] Appl. No.: 636,661

[22] Filed: Apr. 23, 1996

[51] Int. Cl.$^6$ ............................................ A61F 5/37
[52] U.S. Cl. .................... 128/876; 602/19; 5/81.1 T; 5/89.1
[58] Field of Search .................... 128/846, 869, 128/874, 875, 876; 602/5, 19; 5/81.1 T, 89.1; 2/45, 44, 101, 311, 312, 321

[56] References Cited

U.S. PATENT DOCUMENTS

| | | |
|---|---|---|
| 1,035,642 | 8/1912 | Rosse . |
| 1,498,593 | 6/1924 | Waiss . |
| 2,508,795 | 5/1950 | Nielsen . |
| 3,236,234 | 2/1966 | Buckley . |
| 4,139,130 | 2/1979 | Glusker et al. . |
| 4,396,013 | 8/1983 | Hasslinger . |
| 4,449,253 | 5/1984 | Hettinger ........................... 2/94 |
| 4,538,614 | 9/1985 | Henderson ........................... 2/1 |
| 4,981,307 | 1/1991 | Walsh ............................... 2/44 |
| 5,361,418 | 11/1994 | Luzenske .......................... 128/876 |
| 5,514,019 | 5/1996 | Smith ............................. 2/311 |

FOREIGN PATENT DOCUMENTS 2336106  7/1977  France .

*Primary Examiner*—Michael A. Brown
*Attorney, Agent, or Firm*—Michael, Best & Friedrich

[57] ABSTRACT

An article for lifting an incapacitated person includes a thin elongate belt formed of an elastic, flexible rubber-like material. Fasteners are mounted at the ends of the belt for attaching the ends so that the belt may encircle a patient. The width of the belt between its lateral sides is sufficient so that when worn, the belt extends from the waist to the chest of a wearer. A plurality of flexible handles are fixed to the belt in spaced apart relation.

9 Claims, 1 Drawing Sheet

INVALID SUPPORT BELT

BACKGROUND OF THE INVENTION

This invention relates to invalid support belts and more particularly to belts for lifting invalids from beds or wheelchairs.

Incapacitated individuals must, for various reasons, be lifted from time to time for being moved into or out of beds, wheelchairs, or the like. Prior art lifting devices generally comprise bed cranes or leather belts. Once the patient has been lifted to an upright position, other types of belts were often employed in order to aid the patient in walking.

Leather belts or harnesses used for lifting patients were uncomfortable to wear and had a tendency to slide up from the patient's waist area and to twist or torque as the patient was lifted. Such leather belts also could not be worn by the patient in a bath or shower and were difficult to clean. Moreover, prior belts did not retain body heat or support the patient's spinal area.

SUMMARY OF THE INVENTION

It is an object of the invention to provide a new and improved patient lifting belt.

A further object of the invention is to provide a patient lifting belt which is comfortable.

A further object of the invention is to provide a patient lifting belt which is water proof and retains body heat.

Yet another object of the invention is to provide a patient lifting belt in which the lifting forces are not concentrated.

In general terms, the invention comprises an article for lifting an incapacitated person and including a thin elongate belt formed of an elastic, flexible rubber-like material having a pair of ends and lateral sides, fastener means at the ends of the belt for attaching said ends so that the belt may encircle a patient, the width of the belt between its lateral sides being sufficient so that when worn, the belt extends from the waist to the chest of a wearer, and a plurality of flexible handles fixed to the belt in spaced apart relation, the belt transferring the lifting forces over a wide area of the patient's body and extending from the waist to the chest area of the patient.

DETAILED DESCRIPTION OF THE PREFERRED EMBODIMENT

Figure 1:
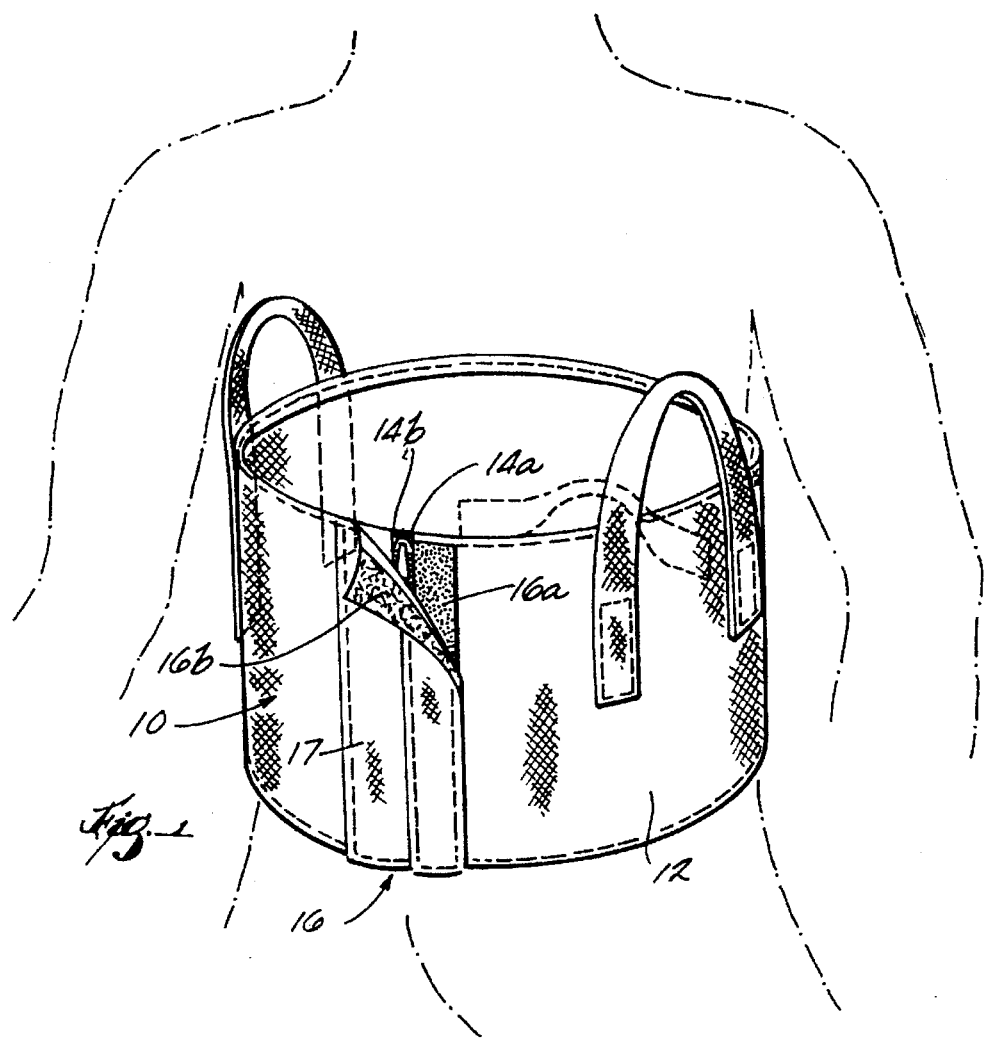
FIG. 1 is a perspective view illustrating how the belt would be worn in use.
Figure 2:
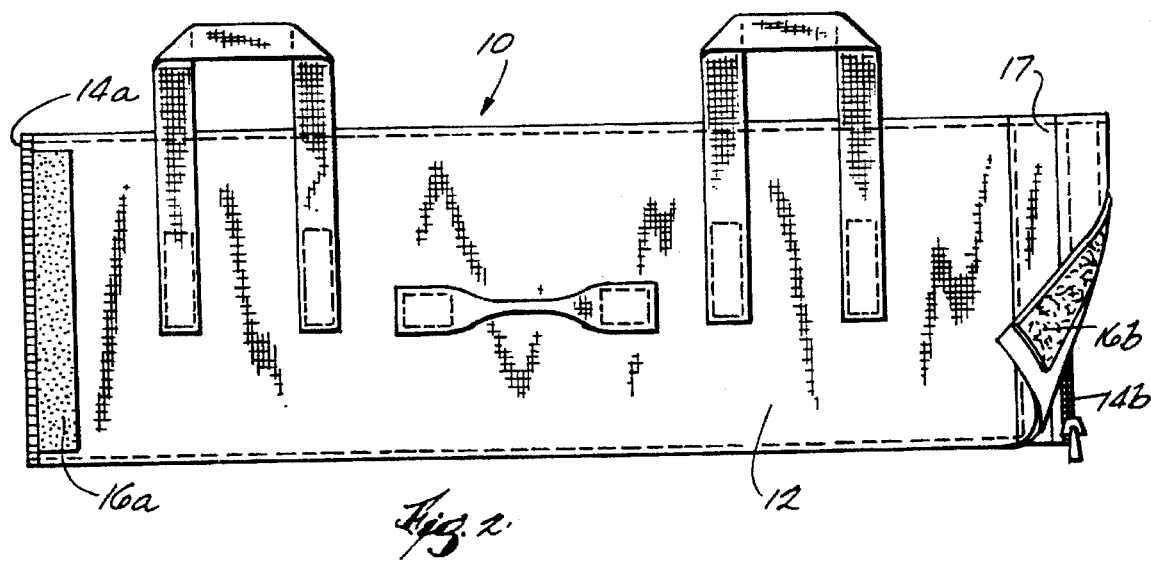
FIG. 2 is a front view of the belt according to the invention.

FIGS. 1 and 2 show the belt 10 according to the invention to include a belt portion 12 which is generally rectangular in plain view. The belt portion 12 is formed of a flexible and elastic material. One example of a material which may be used for the belt portion 12 is a closed cell neoprene rubber such as that sold under the trademark RUBATEX by RUBATEX Corporation. For aesthetic purposes, the outer surface of the belt portion 12 may be covered by a flexible material, such as lycra. However, to minimize the possibility that the belt will slip, the inner surface is preferably not covered.

The opposite ends of the belt portion 10 includes at least one fastener so that the ends may be joined about the chest of the user as shown in FIG. 3. In the preferred embodiment, the fastener comprises a zipper 14 and velcro strips 16a and 16b.

The length of the belt portion 10 should be such that it fits snugly about the wearer without discomfort. It will be appreciated that different sizes are required to fit different sized individuals. The width of the belt portion 12 should be such that it extends approximately from the waist to the breast area of the wearer. A typical width would be about 10 inches.

A plurality of handles are attached to the belt portion in a space apart relation. The handles are formed of strips of a flexible material such as nylon or cotton webbing with opposite ends are sewn to the belt portion 10. In the preferred embodiment, there are three handles 17, 18 and 20. The handles 17 and 18 are positioned on the sides of the belt portion when mounted on the wearer and the third handle 20 is attached to the rear. The stitching for the handles 17, 18 and 20 is indicated by the reference numeral 21.

In the preferred embodiment, the fasteners comprises a zipper 14 having portions 14a and 14b and Velcro fastener 16 consisting of a hook strip 16a attached to one end of the belt portion 12 inwardly of the zipper half 14a and a fabric strip 16b mounted on a flap 22 sewn to the belt portion 12 inwardly of the zipper half 14b so that when the Velcro strip 16b engages the strip 16a, the flap 22 covers the zipper 14. The Velcro adds strength to the connection of the two ends of the belt portion 12 and also covers the zipper which increases comfort to the wearer and minimizes the possibility of the zipper catching on clothing or other articles.

Because the belt portion 12 is formed of a soft flexible resilient material, it can also be worn next to the patient's skin without discomfort. Moreover, the belt can be submerged in water so that it can be worn when the patient is bathing- In addition, the belt 10 can be laundered without damage or change in any of its properties. The closed cell neoprene rubber also acts as a good heat insulator so as to retain the patient's body heat.

The relatively large width of the belt portion 12, which extends from the hips to the breast area of the patient, provides more surface area contact to ensure more stability for safety and is less likely to cause injury or discomfort by distributing the weight of an individual over a larger area. This minimizes the amount of twisting when the patient is lifted to minimize torquing and binding. Moreover, the exposed inner surface of the belt portion 12 minimizes the possibility of slippage to increase patient comfort and safety. Also, because the belt portion 12 is resilient and may be easily stretched, it readily conforms to the patient's body thereby providing comfort and support.

Well only the single embodiment of the invention has been illustrated and described, it is not intended to be limited thereby but only by the scope of the impending claims.

I claim:

1. An invalid support belt including, a belt portion having an inner surface for engaging a patient and an outer surface,
    said belt portion comprising an elongate member having a length sufficient to encircle the upper body of a patient and having a width sufficient to extend from the waist area to the breast area and beneath the arms of the patient,
    said belt portion being composed of a stretchable, elastic and flexible material so that it will readily conform to the body of patient without discomfort,
    fastening means at the opposite ends of the belt portion for securing the support belt around a patient, and
    a plurality of handles having opposite ends fixedly attached in a spaced apart relation on the outer surface of the belt portion, said handles being positioned such that when the belt is in use at least one handle is positioned at each side of the patient and beneath the patient's arms so that a patient wearing the belt can be lifted and assisted.

2. The invalid support belt set forth in claim 1 wherein each handle comprises an elongate, unbroken flexible member fixedly attached at its opposite ends to the belt portion in a spaced-apart relation.

3. The invalid support belt set forth in claim 2 and including a third handle mounted between the pair of handles and positioned to be at the back of a patient when the belt is being worn, the third handle comprising an elongate, unbroken, flexible member fixed at its opposite ends to the belt portion in a spaced apart relation.

4. The invalid support belt set forth in claim 3 wherein said fastening means comprises hook and fabric strips.

5. The invalid support belt set forth in claim 3 wherein said fastening means comprising a zipper.

6. The invalid belt set forth in claim 3 wherein said fastening means includes a zipper and hook and fabric strips mounted to cover said zipper when the support belt is mounted on a patient.

7. The invalid support belt set forth in claim 1 wherein said fastening means comprises hook and fabric strips.

8. The invalid support belt set forth in claim 1 wherein said fastening means comprising a zipper.

9. The invalid belt set forth in claim 1 wherein said fastening means includes a zipper and hook and fabric strips mounted to cover said zipper when the support belt is mounted on a patient.

* * * * *